(12) United States Patent
Hommes et al.

(10) Patent No.: US 9,107,251 B2
(45) Date of Patent: Aug. 11, 2015

(54) DIMMABLE LUMINARY FEATURING COLOUR CHANGE DURING DIMMING

(71) Applicant: KONINKLIJKE PHILIPS N.V., Eindhoven (NL)

(72) Inventors: Vanja Hommes, Assen (NL); Inge Van De Wouw, Antwerp (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/350,678

(22) PCT Filed: Oct. 2, 2012

(86) PCT No.: PCT/IB2012/055266
§ 371 (c)(1),
(2) Date: Apr. 9, 2014

(87) PCT Pub. No.: WO2013/054228
PCT Pub. Date: Apr. 18, 2013

(65) Prior Publication Data
US 2014/0354189 A1 Dec. 4, 2014

Related U.S. Application Data

(60) Provisional application No. 61/546,631, filed on Oct. 13, 2011.

(51) Int. Cl.
*H05B 37/02* (2006.01)
*G04C 19/02* (2006.01)
(Continued)

(52) U.S. Cl.
CPC .............. *H05B 37/029* (2013.01); *G04C 19/02* (2013.01); *G04G 11/00* (2013.01); *H05B 37/0281* (2013.01); *A61M 21/02* (2013.01);
(Continued)

(58) Field of Classification Search
CPC ............... H05B 37/029; A61M 21/00; A61M 2021/0083
USPC ............................ 315/360, 307, 308; 362/801
See application file for complete search history.

(56) References Cited

U.S. PATENT DOCUMENTS 5,327,331 A * 7/1994 Roberts ......................... 362/176
7,280,439 B1 10/2007 Shaddox
7,824,058 B2 11/2010 Inoue

FOREIGN PATENT DOCUMENTS

EP        1808199 A2    7/2007
WO    2006087723 A2    8/2006
(Continued)

*Primary Examiner* — Daniel D Chang
(74) *Attorney, Agent, or Firm* — Yuliya Mathis

(57) ABSTRACT

A wake-up lamp system (100; 1000) comprises: a light source (130) having a nominal light output intensity (Lmax); and a control device (110) for controlling the light source, the control device receiving a clock signal from a clock device (120). The control device, when operating in a wake-up mode, controls the light source such that its light output intensity is gradually increased from a minimum intensity value (Lmin) to a maximum intensity value (Lmu) and such that the color point of the light output is gradually changed to travel a predefined chromaticity path, with the position of the color point on said chromaticity path being set as a function of the light output intensity. Said chromaticity path has a starting point having a color temperature between 400K and 1500K associated with the minimum intensity and an end point having a color temperature higher than 2700K associated with the nominal intensity.

12 Claims, 5 Drawing Sheets

(51) Int. Cl.
*G04G 11/00* (2006.01)
*A61M 21/02* (2006.01)
*A61M 21/00* (2006.01)

(52) U.S. Cl.
CPC .................. *A61M2021/0044* (2013.01); *A61M 2021/0083* (2013.01); *Y02B 20/42* (2013.01)

(56) References Cited

FOREIGN PATENT DOCUMENTS

| WO | 2010035200 A1 | 4/2010 |
| WO | 2011051869 A2 | 5/2011 |

\* cited by examiner

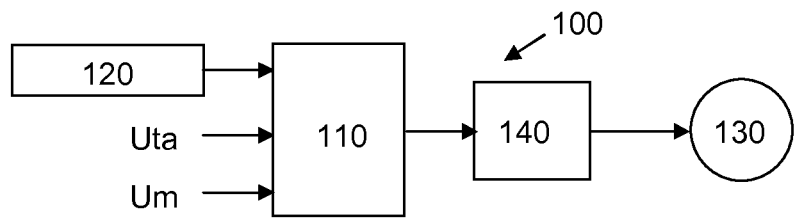
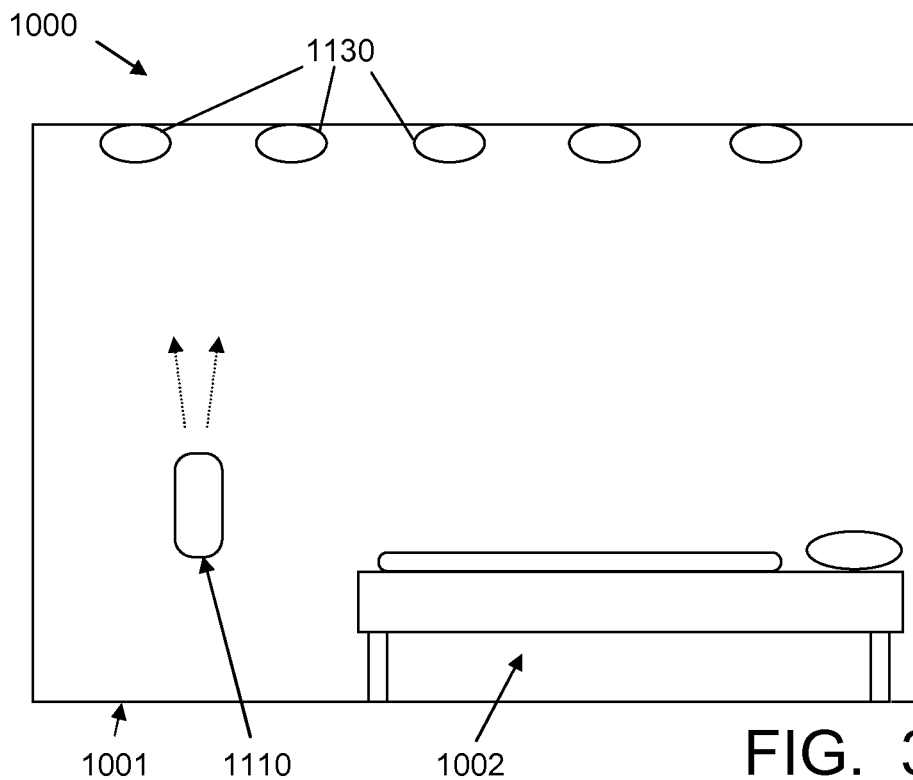
FIG. 3A
FIG. 3B
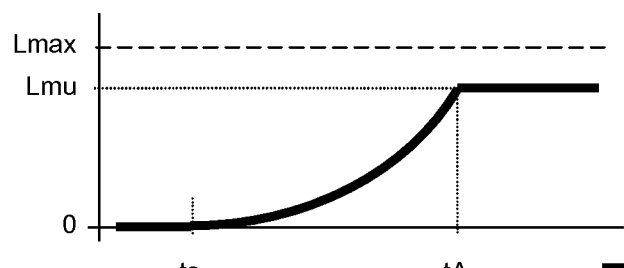
FIG. 4

DIMMABLE LUMINARY FEATURING COLOUR CHANGE DURING DIMMING

This application is the U.S. National Phase application under 35 U.S.C. §371 of International Application No. PCT/IB2012/055266, filed on Oct. 2, 2012, which claims the benefit of U.S. Provisional Application No. 61/546,631 filed on Oct. 13, 2011. These applications are hereby incorporated by reference herein.

FIELD OF THE INVENTION

The present invention relates in general to the field of dimmable luminaries. More particular, the invention relates to luminaries that are capable of simulating natural dusk or dawn, such as for instance wake-up lamps.

BACKGROUND OF THE INVENTION

A wake-up lamp is a device comprising a controllable light source of which the light output intensity can be varied between almost zero and a maximum, which maximum in practice may be in the order of 250-400 Lux at the eyes of the user, it being assumed that the distance between the light source and the user's eyes is a fixed value in accordance with the user's manual. The device is typically associated with an alarm clock, and is intended to wake up people in a comfortable and natural manner by simulating sunrise (or dawn). Starting at a predefined advance time before the set alarm time (typically about 30 minutes earlier), the light source switches on at low intensity, and its intensity is gradually increased until at the alarm time the maximum intensity is reached. Wake-up lamps are known in practice, therefore a further explanation is not needed.

In a simple embodiment, the intensity increase of a wake-up lamp is achieved by simply increasing the power supplied to the light source. Depending on the type of light source, this can be done by increasing the supply voltage (for instance in the case of an incandescent lamp), or it may be necessary to use a more complicated driver design (for instance in the case of an LED). However, the increase of light intensity is only one of the aspects of a successful wake-up lamp. Another important aspect is the colour of the output light. In people's perception, the natural sunrise is associated with a colour change from deep red to yellowish white as the light intensity increases. State of the art wake-up lamps do not show such colour variation, and the result is perceived as "unnatural".

SUMMARY OF THE INVENTION

An objective of the present invention is to provide a wake-up lamp that conveys to its user an improved perception of naturalness and comfort.

FIG. 1 is a graph showing the well-known CIE 1931 chromaticity diagram of the visible spectrum, i.e. the gamut of human vision. Since this diagram is known to persons skilled in the art, the description thereof will be kept brief. Each point within this diagram will be indicated as a colour point. Monochromatic colour points are indicated along the convex border, the other points indicate mix colours. Lines 11 indicate colour points of constant correlated colour temperature (which correlated colour temperature in the following will be abbreviated as CCT), defined by the Planck equation in the range close to the black body line. The black body line is indicated at 12: this line is the collection of colour points travelled by an ideal black body radiator as a function of its temperature between zero and infinity.

Whatever the spectral composition of light reaching the human eye, the chromaticity of the perceived colour can be expressed by only two coordinates x and y. A third coordinate that, together with these two chromaticity coordinates, defines the colour perception is "brightness"; in the case of light sources, "brightness" is related to "intensity" of the light source. Thus, a three-dimensional space can be defined, with independent chromaticity coordinates x, y and intensity coordinate L.

From the above it follows that the light output of a light source can always be represented by one point in said three-dimensional space, and that the chromaticity of this light output can always be represented by the projection of said point onto the xy base plane, i.e. the corresponding colour point.

It is to be noted that when the light outputs of two light sources are mixed, the resulting mixed light has a colour point on a straight line connecting the two colour points corresponding to the two individual light sources, and the precise location on this connecting line is determined by the relative intensities of the two light sources.

By way of example, FIG. 1 contains a point C indicating a possible colour point of an LED. When the light source in a wake-up lamp is a fixed colour LED, varying the power supply to the light source will only result in a corresponding variation of the light output intensity without changing the chromaticity. In other words, point C remains stationary. This is not perceived as being natural.

When the light source in a wake-up lamp is a halogen lamp or an incandescent lamp, varying the power supply to the light source will not only result in a corresponding variation of the light output intensity but will also result in shift of the chromaticity. FIG. 2 is a graph comparable to FIG. 1, illustrating the chromaticity of a standard 12V 100 W halogen lamp of type GY6.355, of which the light output intensity is varied between 0.1 Lux and 300 Lux. The path travelled by the colour point is indicated by thick line 13 between points A and B. It can be seen that this path 13 closely follows a portion of the black body line 12. At 0.1 Lux, the CCT is about 1500 K (point B), and at 300 Lux the CCT is about 2700 K (point A). Although this is already better as compared to constant chromaticity, experiments have shown that the perception is still not natural enough. It is therefore a first objective of the present invention to improve on this aspect.

This objective is met by a new chromaticity path proposed by the present invention. Key features of this chromaticity path are a colour point associated with the minimum intensity value (Lmin) having a correlated colour temperature between 400 K and 1500 K, and a colour point associated with the nominal intensity value (Lmax) having a colour temperature higher than 2700 K.

Even when a chromaticity path is defined, there are different ways such path can be travelled as regards brightness. Experiments have shown that users have a perceptual expectation of a relationship between colour (or CCT) and brightness (i.e. light source intensity). While there is of course some tolerance, deviation from this perceptual expectation will soon lead to the perception that the colour development is unnatural. It is therefore a second objective of the present invention to improve on this aspect.

This objective is met by a new relationship between correlated colour temperature and brightness proposed by the present invention. In this new relationship, the colour change is such that always, for each value of the light output intensity, a step in the light output intensity will be associated with a step in the correlated colour temperature larger than the temperature step would be for a reference black body radiator making the same step in light output intensity.

Further advantageous elaborations are mentioned in the dependent claims.

BRIEF DESCRIPTION OF THE DRAWINGS

These and other aspects, features and advantages of the present invention will be further explained by the following description of one or more preferred embodiments with reference to the drawings, in which same reference numerals indicate same or similar parts, and in which:

FIG. 3A is a block diagram schematically illustrating a wake-up lamp according to the present invention;

FIG. 3B is a block diagram schematically illustrating an illumination system according to the present invention;

FIG. 4 is a graph showing light output intensity of a light source as a function of time for a wake-up lamp;

DETAILED DESCRIPTION OF THE INVENTION

Figure 1:
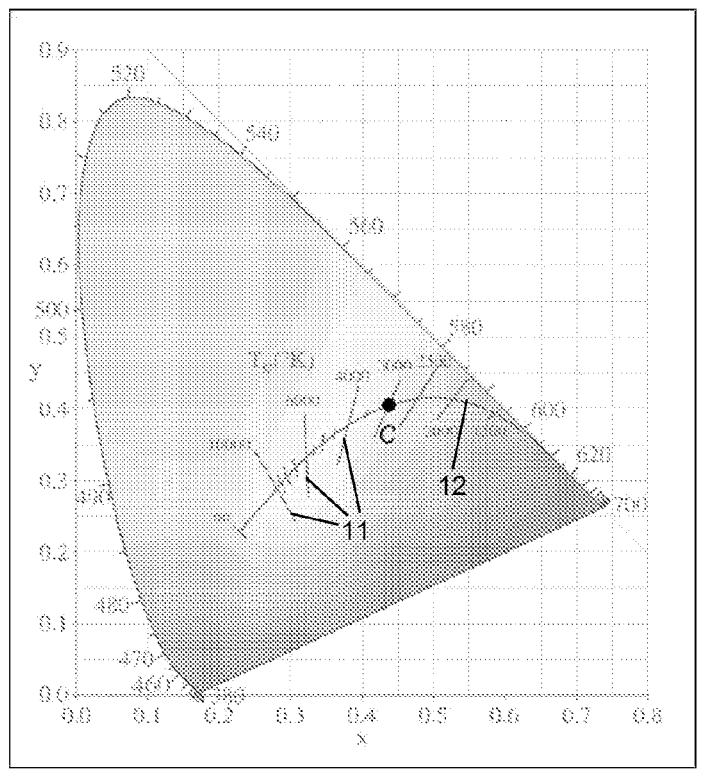
FIG. 1 is a graph showing the CIE 1931 chromaticity diagram of the visible spectrum.

In the following, the inventive features of the wake-up lamp according to the present invention will be explained in more detail. These features involve the travel path through 3D colour space, i.e. xy colour coordinates and brightness. It is noted that it is possible to describe this by specifying x, y and brightness as separate functions of time. However, in the following a more convenient approach will be taken. A chromaticity path will be defined in the xy base plane. A position on the chromaticity path will be defined in terms of CCT, and a relationship will be defined between CCT and brightness (i.e. light source intensity). In this way, the chromaticity path is defined independent of time. The temporal behaviour may be described by describing brightness as a function of time.

FIG. 3A is a block diagram schematically illustrating a wake-up lamp 100 according to the present invention. The wake-up lamp 100 comprises a light source 130, a light source driver 140, a control device 110 for controlling the light source driver 140, and a clock device 120. The control device 110 may for instance comprise a suitably programmed microprocessor, controller, or similar.

The clock device 120 is a device generating a clock signal representing time of day and received by the control device 110; since such clock devices are commonly known, a more detailed description is omitted here. The control device 110 further receives a signal Uta representing a user setting of an alarm time, and a signal Um representing a user setting of a maximum intensity, as will be explained later.

It is noted that the driver 140 is for actually driving the light source 130, i.e. a device for actually generating the power supply for the light source 130 as a supply voltage or a supply current. Since such driver devices are commonly known, a more detailed description is omitted here.

In a typical wake-up lamp assembly, the clock device 120, control device 110, driver 140 and light source 130 will all be integrated in one appliance, accommodated in a common housing. It is, however, also possible that the driver 140 and light source 130 are arranged in a luminary appliance, with the control device 110 being separate, wherein the control device 110 and the driver 140 are adapted for wireless communication. In a variation, the driver 140 may be associated with a local controller, in which case the control device 110 may communicate wirelessly to the local controller. The wireless control device may be implemented as a dedicated hardware device, having the sole purpose of controlling the light source 130, i.e. the driver 140. However, it is also possible that the wireless control device is implemented, for instance in software, in another-purpose handheld device with wireless communication facilities, such as for instance a PDA, a smartphone, a TV remote control. Likewise, the clock device 120 may be mounted with the control device 110, but it is also possible that the clock device 120 is separate and communicates to the control device 110 wirelessly.

With a wireless control device, it is also possible to have an embodiment where the control device controls two or more light sources.

FIG. 3B is a block diagram schematically illustrating an illumination system 1000 according to the present invention. The system 1000 comprises a plurality of illumination light sources 1130 for generating ambient illumination in a room 1001. The room may be a bedroom, with at least one bed 1001. Each light source 1130 may be associated with its own driver, or two or more light sources may share a common driver; in any way, for sake of simplicity, the drivers are not shown in the drawing. The system 1000 further comprises a wireless control device 1110 capable of wirelessly controlling the light sources 1130. The control device 1110 may be similar to the control device 110 discussed above, and may likewise receive a clock signal. The control device 1110 may output one control signal to be received by all light sources, but it is also possible that the control device 1110 outputs two or more control signals for individually controlling the light sources 1130.

The basic operation of the wake-up lamp 100 will be explained with reference to FIG. 4, it being noted that a similar explanation applies to the system 1000. FIG. 4 is a graph showing light output intensity of the light source 130 (vertical axis) as a function of time (horizontal axis). Lmax indicates the nominal or maximum light output intensity of the light source 130. Preferably Lmax is equal to 200 Lux or higher, more preferably 250 Lux or higher, even more preferably 300 Lux or higher, and it is most preferred that Lmax is as high as 400 Lux.

In this respect, it is noted that the intensity in Lux depends on the distance between the light source and the measuring point. In the context of a wake-up lamp, where the purpose of the lamp is primarily to achieve a certain physiological effect on a user, the location of interest is the location of the eyes of the user: these are expected to be at a certain predetermined distance from the lamp, which distance may be specified in the user's manual and may typically be about 50 cm. Where in the context of the present invention the intensity of the light source is specified, this will be specified as measured at such location of interest, i.e. the expected location of the eyes of the user, which location may be indicated as "eye location". The corresponding light intensity may be indicated as "eye intensity", but for sake of simplicity the text will simply refer to "intensity".

It is further noted that the intensity is integrated over all wavelengths of the visible spectrum (for humans), taking account of the human eye's spectral sensitivity as expressed by the photopic sensitivity weighting function.

In the figure, tA indicates an alarm time set by the user. Initially, the light source 130 is off. When the clock signal indicates that a starting time ts has been reached, typically about 30 minutes before tA, the control device 110 switches on the light source 130 at a minimum intensity Lmin close to zero. A practical example of the minimum intensity Lmin is 0.001 Lux.

In a possible embodiment, the user is allowed to define a higher value for the minimum intensity, but this is not illustrated. In the time interval between ts and tA, the control device 110 gradually increases the light output intensity of the light source 130, until at the alarm time tA a user-defined maximum Lmu is reached, which is equal to or lower than the maximum light output intensity Lmax of the light source 130, depending on the user's taste.

The figure shows an exponential dependency between intensity and time. However, apart from the fact that the intensity is growing continuously, the precise relationship between intensity and time is not essential, and the present invention can be practiced with any time-dependency and can be understood without knowledge of the time-dependency.

However, it is preferred that the time-dependency is scaled with the user-selected value of Lmu. With variation of Lmu, the time duration from ts to tA is preferred to remain the same while all intensity values are scaled by the same factor. This can be expressed in a formula as follows. Assume that, when Lmu=Lmax, the time-dependency of the light output intensity L(t) in the time interval from ts to tA is defined by a function f as follows:

$$L(t)[ts:tA]=Lmin+f(t)$$

with f(ts)=0 and f(tA)=Lmax−Lmin.
Then, in general, the light output intensity can be expressed as:

$$L(t)[ts:tA]=Lmin+f(t)\cdot Lmu/Lmax$$

Chromaticity Path

According to an important aspect of the present invention, the colour point of the output light of the wake-up lamp 100 follows a specific predetermined chromaticity path that lies close to or slightly lower than the black body line, as will be explained with reference to FIG. 5.

Figure 2:
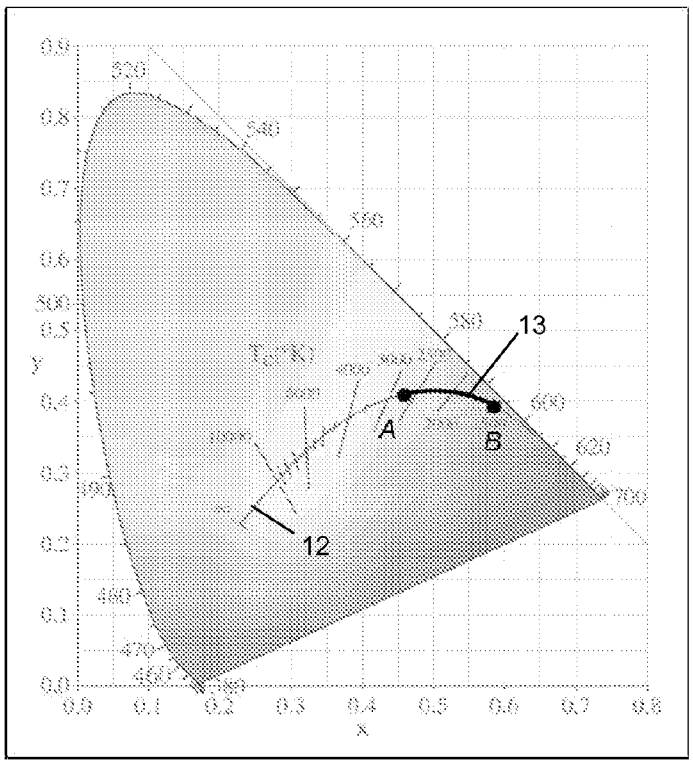
FIG. 2 is a graph comparable to FIG. 1, illustrating the chromaticity of a halogen lamp.
Figure 5:
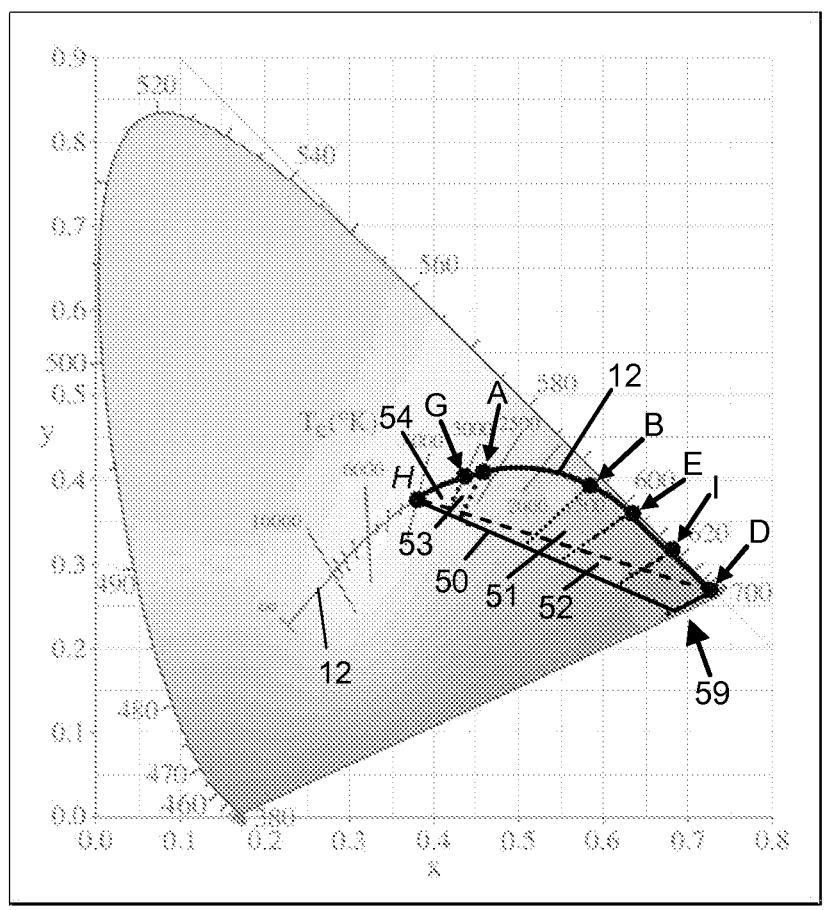
FIG. 5 is a graph comparable to FIG. 2, showing a wake-up operation zone according to the present invention.

FIG. 5 is a graph comparable to FIG. 2, showing the black body line 12 and a straight line portion 50 which intersects the black body line 12 at the point of 4000 K (point H). For sake of convenience, and for reasons that will become clear later, said straight line portion 50 will be indicated as "lower border line". The lower end of said lower border line 50 lies on the purple line (i.e. the line connecting monochromatic blue 380 nm and monochromatic red 700 nm), close to the red point 700 nm: the x-distance between the lower end of said lower border line 50 and the monochromatic red 700 nm point is less than 0.1, preferably less than 0.05. Ideally, the lower end of said lower border line 50 coincides with the monochromatic red 700 nm point.

The black body line 12 and the lower border line 50 form the border lines of a wake-up operation zone 59. Seen in FIG. 5, line 50 is the lower border line of said zone 59 while a portion of the black body line 12, i.e. the portion to the right of the intersection point H, is the upper border line of said zone 59. If the lower end of said lower border line 50 does not coincide with the monochromatic red 700 nm point, as illustrated, a small portion of the purple line is also border line of zone 59. Said wake-up operation zone 59 is defined as the area confined between said border lines, with the border lines included in the wake-up operation zone 59.

The figure also shows several dotted straight lines. Each such dotted line corresponds to a constant CCT close to the black body line and, although the CCT may be defined in a unique manner close to the black body line only, such dotted line is extended to intersect said lower border line 50. For sake of simplicity, these dotted lines will be termed "constant CCT lines" or CCCT lines. These CCCT lines divide the wake-up operation zone 59 into different sections. A first section 51 lies below the CCCT line of 1500 K; i.e. this first section 51 contains all colour points of the wake-up operation zone 59 having a CCT lower than 1500 K. A second section 52 lies below the CCCT line of 1100 K. A third section 53 lies above the CCCT line of 2700 K. A fourth section 54 lies above the CCCT line of 3000 K.

According to the present invention, the behaviour of a wake-up lamp is perceived as being more natural if the CCT range is larger than the CCT range of a dimmed halogen lamp. Thus, the starting point of the preferred chromaticity path, corresponding to the lowest light intensities, is located at a CCT between 400 K and 1500 K, and the end point of the chromaticity path, corresponding to the highest intensities, is located at a CCT higher than 2700 K. Referring to the above-defined sections of the wake-up operation zone 59, the starting point of the chromaticity path is located within the first section 51, and the end point of the chromaticity path is located within the third section 53.

With respect to the starting point of the chromaticity path, it is more preferred that it is located in the CCT range between 800 K and 1100 K, i.e. in the second section 52. It is most preferred that the starting point of the chromaticity path is located at a CCT of 900 K, or within 50 K from this value.

With respect to the end point of the chromaticity path, it is more preferred that it is located in the CCT range between 3000 K and 4000 K, i.e. in the fourth section 54.

Having thus defined the extent of the chromaticity path in terms of its starting point and end point, there are several ways to implement the chromaticity path within the context of the present invention. In a preferred embodiment, the chromaticity path coincides with or closely follows the upper border line of the operation zone 59, i.e. the black body line 12; this chromaticity path is indicated as a thick black line in the chromaticity diagram of FIG. 5. Several points are indicated on this line.

Points A and B are identical to the points A and B mentioned above, corresponding to the CCT range of a dimmed halogen lamp.

Point E indicates the CCT of 1100 K, which for a black body radiator corresponds closely to monochromatic light of 603 nm.

Point D indicates the CCT of 455 K, which for a black body radiator corresponds closely to monochromatic light of 700 nm.

Point I indicates the CCT of 810 K, which for a black body radiator corresponds closely to monochromatic light of 615 nm.

Point G indicates the CCT of 3000 K.

While, as mentioned, the chromaticity path may follow the black body line, it may in practice be difficult to realize such curved line. Then, as an alternative, the chromaticity path may be implemented as a sequence of straight line sections which do not necessarily need to have mutually the same orientation, in which case each individual line section can be realized with two light sources (LEDs) having colour points corresponding to the respective end points of such line section. For instance, with one red LED of 700 nm and one LED of 603 nm, the black body line between points D and E can be approached by a straight line section, while with said LED of 603 nm and one white LED of 4000 K a line section between points E and H can be realized. In that case, the chromaticity path as a whole has a section substantially coinciding with the black body line and a section lying lower than the black body line.

In one preferred embodiment, the chromaticity path comprises at least one path section lying lower than the black body line.

In a more preferred embodiment, the chromaticity path lies entirely lower than the black body line, the starting point and the end point excepted. Again, the path may be curved or angled, but in a simple embodiment the chromaticity path is implemented as a straight line, for instance the broken straight line extending from point D to point H. An advantage of such embodiment is that it can in principle be realized with only two LEDs, one red LED of 700 nm and one white LED of 4000 K. For implementing a path closer to the black body line, a third (or even fourth, fifth, etc) light source such as a halogen lamp or LED can be added.

For defining the way in which the chromaticity path is travelled, it is possible to define separate functions x(L) and y(L) that describe the respective colour coordinates as a function of intensity. However, this requires two parameters. Once the chromaticity path is defined, it is possible to define the position on this path by one single parameter, and a suitable parameter is the correlated colour temperature T. Therefore, in the following, positions on the chromaticity path will be defined by specifying the correlated colour temperature T of such position, and the operation of the wake-up lamp according to the present invention will be defined by specifying the correlated colour temperature T as a function of the light output intensity L. It is repeated that the time-dependency can be defined by defining the light output intensity L as a function of time, but this is not essential for practising the present invention.

According to an important aspect of the present invention, the control device 110 is designed to control the correlated colour temperature T of the light output of the light source 130 as a function of the light output intensity L. This will be explained with reference to FIG. 6, which is a graph showing colour temperature T (vertical axis) as a function of light output intensity L (horizontal axis). It is noted that the horizontal axis has a logarithmic scale. Curve 61 represents the relationship between colour temperature T and light output intensity L for a black body radiator reaching a colour temperature 2800 K at an illuminance of 300 lux, measured at eye location: it can be seen that this curve is largely concave with the concave side up. The broken lines 62 and 63 correspond to black body radiators of 2600 K and 3000 K, respectively, also at 300 lux.

Curves 65 represent the preferred relationship between colour temperature T and light output intensity L for the wake-up lamp 100 according to the present invention, for different values of Lmu. These curves will be indicated as "dawn curves".

These dawn curves 65 have different inventive features, as follows.

Minimum Colour Temperature

Figure 6:
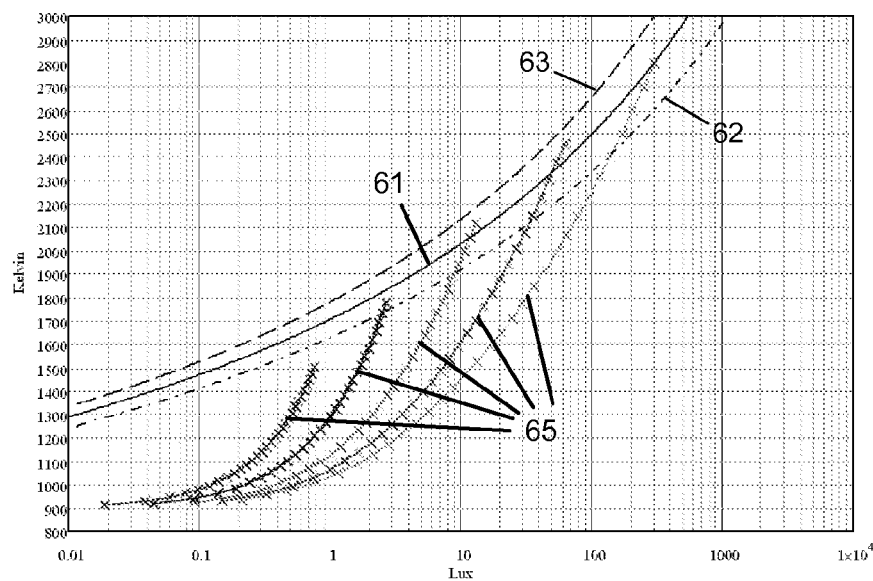
FIG. 6 is a graph showing colour temperature as a function of light output intensity according to the present invention.

At the lowest intensity Lmin, i.e. at time ts, the correlated colour temperature is always lower than the colour temperature of a black body at the same intensity Lmin. It is preferred that the correlated colour temperature at Lmin is within the range of 800 K and 1100 K. It is preferred that this lowest colour temperature is constant, irrespective of Lmin. Most preferably, this lowest colour temperature is approximately equal to 900 K, which is depicted in FIG. 6.

Maximum Colour Temperature

Figure 7:
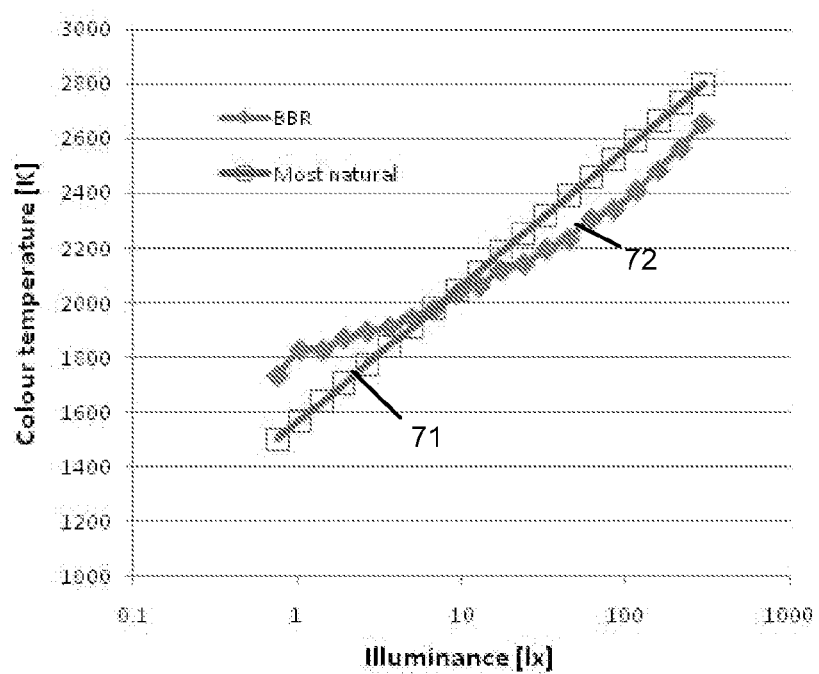
FIG. 7 is a graph showing the maximum colour temperature as a function of maximum light intensity.

The maximum colour temperature depends on Lmu. For higher values of Lmu, the corresponding maximum colour temperature increases. FIG. 7 is a graph showing maximum colour temperature Tmax (vertical axis) as a function of maximum light output intensity Lmu (horizontal axis). It is noted that the horizontal axis has a logarithmic scale. Line 71 is a line containing all points of maximum light output Lmu and corresponding maximum colour temperature Tmax, which are end points of dawn curves 65 in FIG. 6. This line 71 preferably is a straight line, as shown. For sake of comparison, a black body dawn line 72 similar to line 61 of FIG. 6 is shown here for reference (in this case, the reference dawn line 72 corresponds to a black body radiator of 2700 K at 300 lux). In any case, for low values of Lmu the corresponding maximum colour temperature is lower than the black body temperature at that light intensity. Line 71 is steeper than the black body dawn line 72, intersecting the black body dawn line 72 at a temperature value between 1900 K and 2100 K, preferably at a temperature value of about 2000 K. For values of Lmu higher than said point of intersection, the corresponding maximum colour temperature is higher than the black body temperature at that light intensity.

In an initiation mode, the control device 110 allows the user to manually vary the light output intensity, and the control device 110 will always set the correlated colour temperature in accordance with line 71. Thus, the user can be said to travel the line 71 to select an end point of his dawn curve.

Shape

The shapes of the curves are similar, except for a scaling factor. The precise shapes of the curves are not essential. What is important is that, in those settings where the maximum light output Lmu is such that the corresponding maximum colour temperature is above the black body colour temperature at the same intensity Lmu, the colour temperature is nevertheless lower than the corresponding black body colour temperature for at least 90% of the range between Lmin and Lmu, i.e. for at least all values of the intensity between Lmin and Lmin+0.9·(Lmu−Lmin).

It is further to be noted that a dawn line associated with a higher value of Lmu lies always higher than a dawn line associated with a lower value of Lmu, except perhaps for very low values of the light output intensity (lefthand side in FIG. 6) where the CCT may be almost independent from Lmu.

Temperature Range

When varying from Lmin to Lmu, the correlated colour temperature changes over a larger range than a black body radiator would do when varied from Lmin to Lmu.

Colour Variation

Assume that the light output of the wake-up lamp 100 has a certain light output intensity L and a certain correlated colour temperature Tw. At that same intensity L, a black body radiator would have a correlated colour temperature Tb. Assume that the control device 110 changes the light output intensity to L+ΔL. This involves a change in the colour temperature from Tw to Tw+ΔTw in accordance with the applicable dawn line 65. For said black body radiator, when the light output intensity would be likewise changed to L+ΔL, the correlated colour temperature would change to Tb+ΔTb. At all times, ΔTw is larger than ΔTb. In other words, dT/dL(w) for the inventive wake-up lamp 100 is always larger than dT/dL(b) for a black body radiator at the same light output intensity L. Experiments have shown that consumers perceive such behaviour as more natural as compared to a black body radiator.

However, this consumer's perception is less critical at lower levels of the light output intensity. In this respect, reference is made to FIG. 6, where it can be seen that for low levels of the light output intensity the colour temperature hardly changes as a function of the light output intensity anyway. Since such small temperature variations at such small intensity values are hardly noticeable, it is acceptable is in those ranges the ideal dawn line 65 is approximated by a horizontal line. In other words, in such embodiment there exists a threshold intensity level Lth, which is selected to be low: for instance Lth is equal to 1 Lux or lower; wherein $dT/dL(w)=0$ for $L<Lth$ and $dT/dL(w)>dT/dL(b)$ for $L>Lth$.

Figure 8:
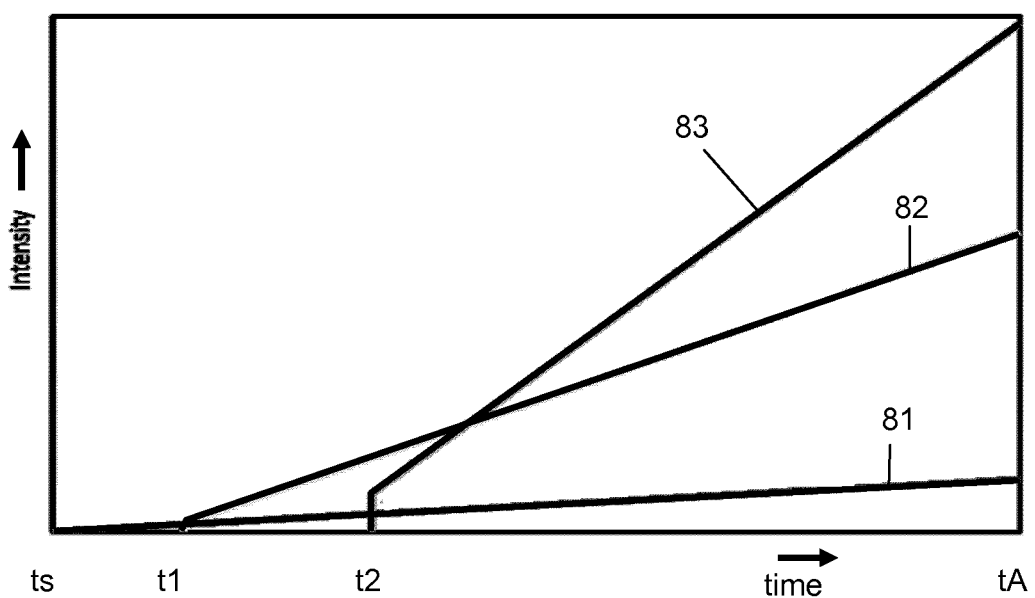
FIG. 8 is a graph illustrating the operation of a particular embodiment of the wake-up lamp according to the present invention.

In an embodiment, the light source 130 comprises three individually controllable light source elements having mutually different colour points. In a specific example, the light source 130 comprises a single medium power red LED of 40 mA nominal current, a single high power amber LED of 700 mA nominal current, and an array of three high power white LEDs of 700 mA nominal current each. FIG. 8 is a graph schematically illustrating the operation of this embodiment, wherein the horizontal axis represents time and the vertical axis represents light output intensity, which is approximately proportional to LED current.

Before time Ts, all LEDs are off. At time ts, the control device 110 starts the red LED at a minimum power setting for this LED. With time, the power supply to this LED is increased, which increase may be gradual or stepwise. Line 81 indicates the light output intensity of this red LED as a function of time. It can be seen that the light output intensity increases, but it will be clear that the CCT remains constant.

At a certain first time t1, when the light output intensity of the red LED has reached the value Lth, the control device 110 starts the amber LED at a minimum power setting for this LED. With time, the power supply to this LED is increased, which increase may be gradual or stepwise. Line 82 indicates the light output intensity of this amber LED as a function of time. The CCT as well as the light output intensity of the overall output light will make a small step at time t1, but this is masked by the output light from the red LED. It can be seen that the light output intensity of the amber LED rises faster than the light output intensity of the red LED, so that the colour point of the overall output light shifts from pure red towards amber, i.e. the CCT associated with the colour point of the overall output light increases.

At a certain second time t2, the control device 110 starts the white LEDs at a minimum power setting for these LEDs. With time, the power supply to these LEDs is increased, which increase may be gradual or stepwise. Line 83 indicates the light output intensity of these white LEDs as a function of time. The CCT as well as the light output intensity of the overall output light will make a small step at time t2 (which is shown exaggeratedly large in FIG. 8), but this is masked by the output light from the amber LED. It can be seen that the light output intensity of the white LEDs rises faster than the light output intensity of the amber LED, so that the colour point of the overall output light shifts from amber towards white, i.e. the CCT associated with the colour point of the overall output light increases further.

In FIG. 8, all LEDs reach their maximum light output intensity at time tA. In an alternative embodiment, it is possible that the red LED reaches its maximum light output intensity earlier, for instance as early as time t1. After that, i.e. between t1 and tA, the light output intensity of the red LED may be kept constant, or may even be reduced back to zero. Likewise, in order to approach a CCT closer to white, the light output intensity of the amber LED may be reduced as from a certain time, even to such extent that this light output intensity reaches zero at time tA.

While the invention has been illustrated and described in detail in the drawings and foregoing description, it should be clear to a person skilled in the art that such illustration and description are to be considered illustrative or exemplary and not restrictive. The invention is not limited to the disclosed embodiments; rather, several variations and modifications are possible within the protective scope of the invention as defined in the appending claims. For instance, where the description explains that the wake-up lamp comprises a light source having a certain colour point, for instance an LED, such light source may in fact consist of two or more light source elements for increased light output.

In the above, the operation of the wake-up lamp is described for the wake-up mode. However, the device can also operate in a reverse mode, wherein the light output is slowly dimmed, to be used when going to sleep. In such reverse mode, the light output starts at maximum and the dawn curve described above is travelled in the opposite direction, but apart from the time-reversal all explanations remain the same.

Further, the device may be capable of operating in a manual mode, in which the control device 110 allows the user to manually set or vary the light output intensity, and in which the control device 110 will set the control the light source such that the colour point of the light output is set on the predetermined chromaticity path with the correlated colour temperature set in accordance with the function of the light output intensity as expressed by the appropriate dawn line 65.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

In the above, the present invention has been explained with reference to block diagrams, which illustrate functional blocks of the device according to the present invention. It is to be understood that one or more of these functional blocks may be implemented in hardware, where the function of such functional block is performed by individual hardware components, but it is also possible that one or more of these functional blocks are implemented in software, so that the function of such functional block is performed by one or more program lines of a computer program or a programmable device such as a microprocessor, microcontroller, digital signal processor, etc.

The invention claimed is:

1. Wake-up lamp system, comprising:
    a light source for producing light output with a light output intensity and a colour point in a CIE 1931 xy chromaticity diagram, the light source having a nominal light output intensity (Lmax);
    a clock device generating a clock signal;
    and a control device for controlling the light source, the control device being coupled to receive said clock signal from the clock device;
    wherein the control device is adapted to operate in a wake-up mode;

wherein the control device, when operating in the wake-up mode, controls the light source such that the light output intensity is made to gradually increase from a minimum intensity value (Lmin) to a maximum intensity value (Lmu) and such that the colour point of the light output is made to travel a predefined chromaticity path in said chromaticity diagram, said chromaticity path having a starting point associated with the minimum intensity value (Lmin) and an end point associated with the nominal intensity value (Lmax), the control device being designed to set a position of the colour point on said chromaticity path as a function of the light output intensity;

wherein said starting point has a colour temperature between 400 K and 1500 K and wherein said end point has a colour temperature higher than 2700 K;

wherein each colour point on said chromaticity path has an associated colour temperature T, with a maximum colour temperature Tmax associated with the nominal intensity value (Lmax), and wherein the control device is designed, when varying the light output intensity of the light source, at least for values of the light output intensity higher than a predefined threshold level Lth, to simultaneously vary the position of the colour point on said chromaticity path such that a derivative dT/dL(L) of the colour temperature T of the light output is derivative dT/dL(L) for a black body radiator having at said nominal intensity value (Lmax) a colour temperature equal to said maximum colour temperature Tmax.

2. Wake-up lamp system according to claim 1, wherein said starting point has a colour temperature between 800 K and 1100 K, while preferably said starting point has a colour temperature in a range of 850-950 K.

3. Wake-up lamp system according to claim 1, wherein said end point has a colour temperature between 2700 K and 4000 K, while preferably said end point has a colour temperature in a range of 2750-3200 K.

4. Wake-up lamp system according to claim 1, wherein said predefined chromaticity path lies within a chromaticity zone in said chromaticity diagram, said chromaticity zone having an upper border line formed by a portion of a black body line, the black body line being defined as the collection of colour points travelled by an ideal black body radiator in said chromaticity diagram as a function of its temperature between zero and infinity, and said chromaticity zone having a lower border line formed by a straight line between chromaticity points [x,y=0.38,0.38] and [x,y=0.68,0.24], said border lines being included in said chromaticity zone.

5. Wake-up lamp system according to claim 4, wherein at least a section of said predefined chromaticity path, and preferably the entire chromaticity path, coincides with a part of the black body line.

6. Wake-up lamp system according to claim 4, wherein at least a section of said predefined chromaticity path, and preferably the entire chromaticity path with the exception of starting point and end point, lies within said chromaticity zone lower than said upper border line.

7. Wake-up lamp system according to claim 4, wherein said predefined chromaticity path comprises at least one straight line section, while preferably the entire chromaticity path is a straight line.

8. Wake-up lamp system according to claim 1, wherein each colour point on said chromaticity path has an associated colour temperature T, with a maximum colour temperature Tmax associated with the nominal intensity value (Lmax), and wherein at least for 90% of the range of light output intensities between the minimum intensity value (Lmin) and the maximum intensity value (Lmu), the colour temperature T(L) of the light output of the wake-up lamp is lower than the colour temperature T(L) of a black body radiator having at said nominal intensity value (Lmax) a colour temperature equal to said maximum colour temperature Tmax.

9. Wake-up lamp system according to claim 1, wherein the minimum intensity value (Lmin) is equal to 1 Lux or less, preferably 0.001 Lux or less.

10. Wake-up lamp system according to claim 1, wherein the nominal light output intensity (Lmax) is equal to 150 Lux or higher, more preferably 250 Lux to 400 Lux, and most preferably between 300 and 350 Lux.

11. Wake-up lamp system according to claim 1, wherein the light source comprises at least one red LED having a colour point equal to the starting point of the chromaticity path, and wherein the light source further comprises:
at least one white LED having a colour point equal to the end point of the chromaticity path;
or
at least one PL lamp or halogen lamp;
or
at least one black body radiator, and optionally at least one white LED having a colour point equal to the end point of the chromaticity path.

12. Wake-up lamp system according to claim 1, wherein the light source comprises at least one red light source element having a colour point equal to the starting point of the chromaticity path, at least one amber light source element, and at least one white light source element;
wherein the control device is designed to:
in a first stage between time is and time t1, increase the light output intensity of the red light source element while keeping the other light source elements off;
in a second stage between time t1 and time t2, increase the light output intensity of the amber light source element while keeping the white light source element off;
in a second stage between time t2 and time tA, increase the light output intensity of the white light source element.

* * * * *